United States Patent
Engelking et al.

(10) Patent No.: US 7,456,392 B2
(45) Date of Patent: Nov. 25, 2008

(54) USE OF ULTRAPHOBIC SURFACES HAVING A MULTITUDE OF HYDROPHILIC AREAS FOR ANALYZING SAMPLES

(75) Inventors: Joachim Engelking, Neustadt (DE); Karsten Reihs, Cologne (DE); Eckhard Nordhoff, Berlin (DE); Martin Muller, Berlin (DE)

(73) Assignee: Qiagen GmbH, Hilsden (DE)

( * ) Notice: Subject to any disclaimer, the term of this patent is extended or adjusted under 35 U.S.C. 154(b) by 218 days.

(21) Appl. No.: 10/505,616

(22) PCT Filed: Feb. 24, 2003

(86) PCT No.: PCT/EP03/01858

§ 371 (c)(1),
(2), (4) Date: Aug. 10, 2005

(87) PCT Pub. No.: WO03/071274

PCT Pub. Date: Aug. 28, 2003

(65) Prior Publication Data

US 2005/0279927 A1  Dec. 22, 2005

(30) Foreign Application Priority Data

Feb. 22, 2002 (DE) ................. 102 07 614
Nov. 26, 2002 (DE) ................. 102 55 276

(51) Int. Cl.
*B01L 3/00* (2006.01)

(52) U.S. Cl. ............. 250/288; 250/281; 250/282; 428/411.1

(58) Field of Classification Search ........... 250/288, 250/281, 282; 428/411.1, 161, 141, 164, 428/172

See application file for complete search history.

(56) References Cited

U.S. PATENT DOCUMENTS

| | | | | |
|---|---|---|---|---|
| 5,674,592 A * | 10/1997 | Clark et al. | ............... | 428/161 |
| 6,287,872 B1 * | 9/2001 | Schurenberg et al. | ....... | 436/181 |
| 6,952,011 B2 * | 10/2005 | Brown et al. | ............... | 250/288 |
| 6,956,209 B2 * | 10/2005 | DiCesare | ............... | 250/288 |
| 7,019,288 B2 * | 3/2006 | Becker | ............... | 250/288 |
| 7,285,331 B1 * | 10/2007 | Reihs et al. | ............... | 428/411.1 |

(Continued)

FOREIGN PATENT DOCUMENTS

DE  196 28 928 A1  1/1998

(Continued)

OTHER PUBLICATIONS

Chemical Analysis of Inorganic and Organic Surfaces and Thin Films by Static Time-of-Flight Secondary Ion Mass Spectrometry (TOF-SIMS), Alfred Benninghoven, Angew. Chem. Int. Ed. Engl. 1994, 33, 1023-1043.

(Continued)

*Primary Examiner*—Jack I Berman
*Assistant Examiner*—Michael J Logie
(74) *Attorney, Agent, or Firm*—Perman & Green, LLP

(57) ABSTRACT

The invention relates to the use of surfaces having hydrophilic and/or oleophilic areas, each of which being completely surrounded by the ultraphobic areas, for analyzing samples. The invention also relates to a method for precisely dosing liquids without contaminating them.

14 Claims, 5 Drawing Sheets

U.S. PATENT DOCUMENTS

| 2002/0142351 | A1* | 10/2002 | Diamond | 435/7.1 |
|---|---|---|---|---|
| 2003/0108449 | A1* | 6/2003 | Reihs et al. | 422/99 |
| 2004/0197921 | A1* | 10/2004 | Schurenberg et al. | 436/43 |
| 2005/0130222 | A1* | 6/2005 | Lee | 435/7.1 |
| 2006/0016984 | A1* | 1/2006 | Finch et al. | 250/288 |

FOREIGN PATENT DOCUMENTS

| DE | 197 54 978 A1 | 7/1999 |
|---|---|---|
| DE | 198 60 136 A1 | 6/2000 |
| DE | 199 10 809 A1 | 9/2000 |
| DE | 199 23 761 C1 | 2/2001 |
| DE | 100 26 299 A1 | 11/2001 |
| DE | 100 43 042 A1 | 3/2002 |
| DE | 102 07 615 A1 | 9/2003 |
| EP | 1 053 784 A2 | 11/2000 |
| WO | WO 96/04123 | 2/1996 |
| WO | WO 96/21523 | 7/1996 |
| WO | WO 96/34697 | 11/1996 |
| WO | WO 98/23549 | 6/1998 |
| WO | WO 98/45406 | 10/1998 |
| WO | WO 00/38845 | 7/2000 |
| WO | WO 00/39051 | 7/2000 |
| WO | WO 00/39239 | 7/2000 |
| WO | WO 00/39240 | 7/2000 |
| WO | WO 00/39368 | 7/2000 |
| WO | WO 00/39369 | 7/2000 |
| WO | WO 01/26797 A2 | 4/2001 |
| WO | WO 01/58688 A1 | 8/2001 |

OTHER PUBLICATIONS

"Radio frequency GDOES depth profiling analysis of a B-doped diamond film deposited onto Si by microwave plasma CVD", K. Shimizu, et al., Surf. Interface Anal. 2002; 33:35-40.

"Multiple Interference of Anthracyclines with Mitochondrial Creatine Kinases: Preferential Damage of the Cardiac Isoenzyme and Its Implications for Drug Cardiotoxicity", Malgorzata Tokarska-Schlattner, et al., Molecular Pharmatology, vol. 61, No. 3, pp. 516-523, 2002.

"Diagnosis of Fragile X Syndrome by Southern Blot Hybridization Using a Chemiluminescent Probe: A Laboratory Protocol", Bert Gold, PhD., et al., Molecular Diagnosis vol. 5, No. 3, pp. 169-178, 2000.

"DNA Arrays, Technologies and Experimental Strategies", Elena V. Grigorenko, Life Sciences/Neuroscience, Table of Contents, 2002.

"Alterations in interprotein interactions between translation initiation factors assessed by fluorescence resonance energy transfer", Scot R. Kimball, et al., The International Journal of Biochemistry & Cell Biology 33 (2001) 797-806.

"Novel Diode Laser-compatible Fluorophores and Their Application to Single Molecule Detection, Protein Labelling and Fluorescence Resonance Energy Transfer Immunoassay", Bernhard Oswald, et al., Photochemistry and Photobiology, 2001, 74(2), pp. 237-245.

"A cGMP-Dependent Protein Kinase Assay for High Throughput Screening Based on Time-Resolved Fluorescence Resonance Energy Transfer", Benjamin Bader, et al., Journal of Biomolecular Screening, vol. 6, No. 4, pp. 255-264, 2001.

"Single molecule DNA sequencing in submicrometer channels: state of the art and future prospects", M. Sauer, et al., Journal of Biotechnology 86 (2001) 181-201.

"MALDI MS as a new method for the analysis of nucleic acids (DNA and RNA) with molecular masses up to 150 kDa", E. Nordhoff, et al., pp. 86-101, 1996.

* cited by examiner

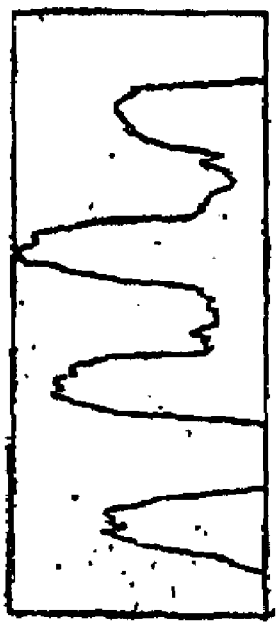
Figure 2c
Figure 2
Length/mm
Intensity/RFU 100
Figure 2b
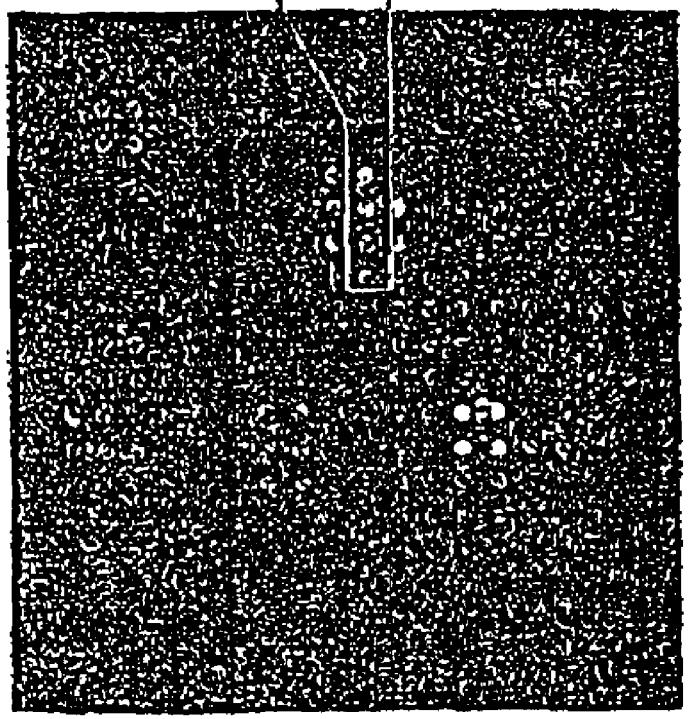
Figure 2a

USE OF ULTRAPHOBIC SURFACES HAVING A MULTITUDE OF HYDROPHILIC AREAS FOR ANALYZING SAMPLES This application is the National Stage of International Application No. PCT/EP03/01858, International Filing Date, Feb. 24, 2003, which designated the United States of America, and which international application was published under PCT Article 21(2) as WO Publication No. WO 03/071274 A1 and which claims priority from German Application No. DE 102 07 614.6 filed Feb. 22, 2002 and German Application No. DE 102 55 276.2 filed Nov. 26, 2002.

The invention relates to the use of surfaces with hydrophilic and/or oleophilic areas, completely surrounded by ultraphobic areas for mass spectrometric and/or optical analysis of samples. The invention relates to a procedure for exact, contamination free dosing of liquids.

The analysis of samples, for instance, as is performed in the fields of bioactive compound chemistry or biological research and production, increasingly depends on mass spectrometry and/or optical detection procedures. For the analysis of the biomolecules found in these samples, the use of matrix-assisted laser desorption/ionisation mass spectrometry (MALDI) is preferable.

With mass spectrometric analysis, as a rule, the liquid droplets are placed in a cleaned sample container, for instance, pipetted, and then analysed. This sample container consists, pursuant to the state of the art, of glass or metal and the wettable surface of the liquid droplets corresponds approximately to the diameter of the liquid droplets. An additional sample container is described in DE 197 54 978 A1, and is characterized by a comparatively hydrophobic surface of Teflon® or graphite, which is incorporated in the hydrophilic base area. The sample container, pursuant to the state of the art, has, however, the disadvantage, that the analysis, conducted by these means, is often comparatively imprecise, since impurities contained in the surface of the sample container and the material transport phenomenon between the surface of the sample container and the liquid droplets influences the measurement.

With the optical analysis procedure, DNA probes, for instance, in the form of liquid droplets, are placed in a sample container and, for instance, mixed with a fluorescence marker and then optically analysed. The sample container, as a rule, is created of glass, so that the liquid droplets, with a comparatively large surface, lay on the glass surface, wherein with the optical analysis, a background signal is produced, that influences the quality of the analysis. The selfsame holds true for Teflon® surfaces, incorporated in the hydrophilic base area. These surfaces are, for instance, disclosed in DE 197 54 978 A1. Hydrophobic surfaces with hydrophilic microvolume, in which liquid may be collected, are known under WO 98/45406. These surfaces, in like manner, exhibit the aforesaid disadvantages.

The subject of the patent is the development of a procedure, with which the mass spectroscopic or optical analysis of samples may be improved.

This task has been solved, pursuant to the distinctive characteristics of the present invention, through the use of surfaces with hydrophilic and/or oleophilic areas, respectively, completely surrounded by ultraphobic areas for mass spectrometric analysis of samples.

BRIEF DESCRIPTION OF THE DRAWINGS

FIG. 2 shows the results of Example 4a where FIGS. 2a, b, and c depict the analysis of the liquid droplets obtained from Example 4a analyzed with a Genepix 4000 B device. In FIG. 2a, the sample carrier is depicted. The light points represent liquid droplets, which are immobilized on the hydrophilic anchors. In FIG. 2b, four liquid droplets and their surroundings are depicted in enlarged scale The more intensive and detailed analysis of the fluorescence image, illustrated by FIG. 2b, is represented in the form of a histogram, with related pixel values alongside the light regions in FIG. 2c

FIG. 4a depicts a cross section of surface 2 of a sample carrier 6. FIG. 4b illustrates the manner in which a water droplet 4, which hangs from a pipette or a rod, is brought in contact with the hydrophilic area where through the ultraphobicity of surface 5, which completely surrounds the hydrophilic area 3, the contact angle of the water droplet 4 is so large, that it touches only the hydrophilic area 3 and not the ultraphobic area 5. FIG. 4c shows the situation after the droplet 4 of the hydrophilic area is removed.

Figure 1:
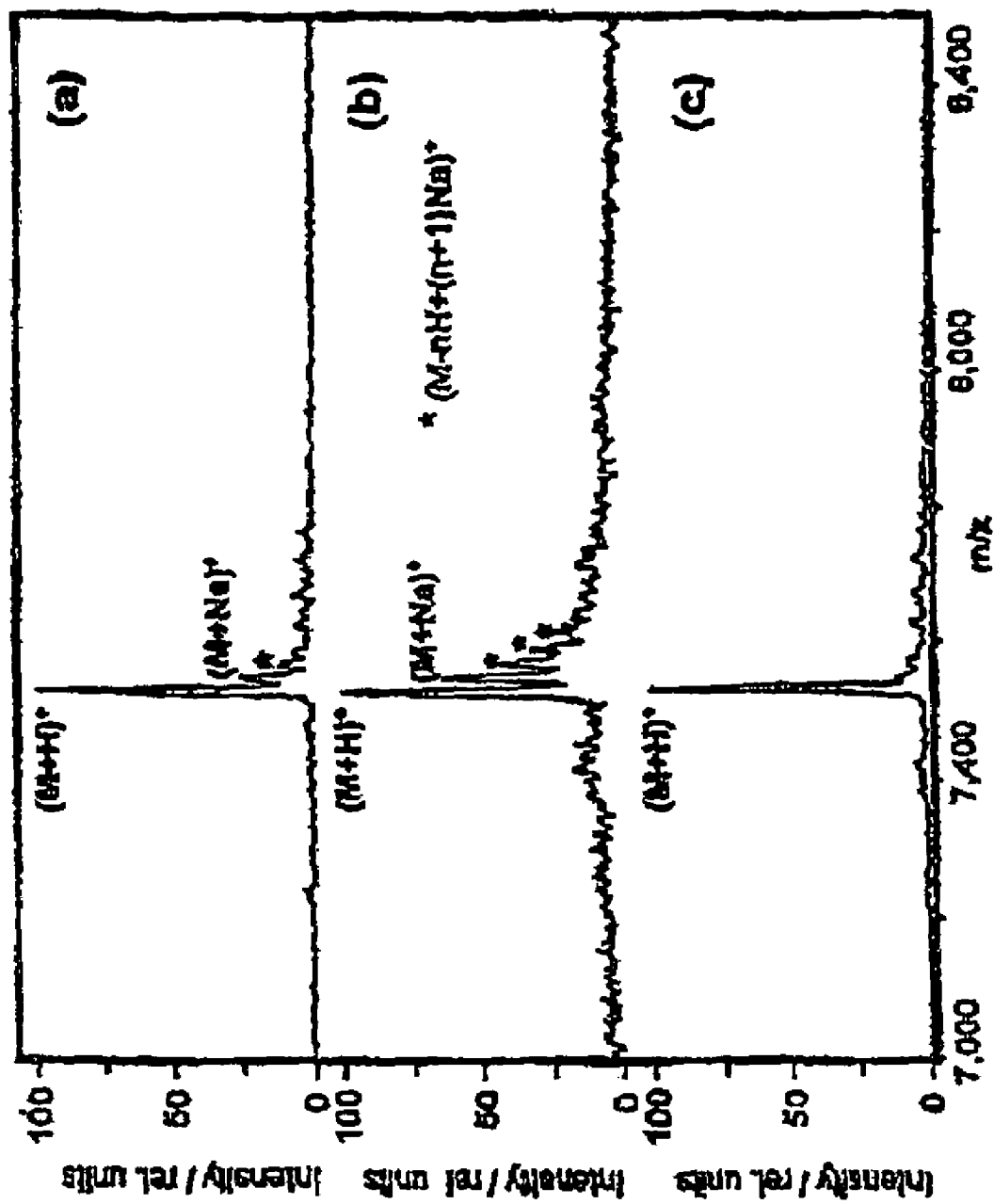
FIG. 1 shows, respectively, the representative results of experimental procedures 3a-c, whereby the letters associated with the spectra correspond to the letters of Example 3.

The surface may form a portion of any arbitrary surface formation or be thereupon arranged. Preferably, the surface formation will be a surface structure in the form of a plate, with an even surface, and particularly preferably, the sample container surface has no indentations. Most preferably, a film, the surface of which exhibits respectively hydrophilic and/or oleophilic areas, completely surrounded by ultraphobic areas, will constitute the surface formation, pursuant to the invention.

In another preferred sample embodiment of the present invention, the surface is planar. Planar, in the sense of the invention, implies that the surface exhibits the necessary ultraphobic properties in terms of surface topography, such that there is no microvolume in which liquid may be collected. Planar surfaces have, in particular, the advantage, that the manufacture is simple and that the liquid droplets need not, as known pursuant to the state of the art, be compressed in a microvolume or in a base area. In addition, with planar surfaces, their influence on the liquid droplets lying thereon is very small.

The samples, which are to be analysed, pursuant to the invention, with the procedure therein described, may also contain arbitrary substances, accessible to a mass spectrometric analysis. Preferably, the sample will contain, however, at least one biomolecule and/or biological material, very preferably nucleic acids, nucleic acid analogs, Spiegelmers, aptamers, ribozymes, peptides, polypeptides, proteins and/or antibodies. Preferably contained in the sample, in addition to the to be analysed substances, will be at least one additional reagent. Furthermore, the to be analysed substances are preferably first to be placed in the hydrophilic and/or oleophilic areas and, then, preferably pressurized with at least one additional reagent, in order to analyse the reaction of the respectively to be analysed substance with the respective reagent. Conversely, in addition, it is naturally conceivable first to dose the hydro- and/or oleophobic areas with different reagents and thereupon to pressurize these areas with the substances to be analysed.

Most preferably, the MALDI procedure is that which is suggested to be used for these purposes, pursuant to the invention. With this procedure, preferably, in particular, biomolecules and/or biological material are to be mixed with a matrix substance and then the hydro- and/or oleophilic areas to be, thus, dosed with this sample, for instance, using a pipette. This sample, thereupon, is to be dried at the surface. The crystals formed in consequence are, for instance, to be analysed with a MALDI TOF mass spectroscope in linear or in reflector mode. Details to this procedure may be obtained in Nordhoff et. al., "MALDI MS as a new method for the analysis of nucleic acid (DNA and RNA) with molecular masses up to 150,000 Dalton, application of mass spectrometric methods to plant science research", Oxford University Press, (1996) Page 86 101, which is herewith listed as a reference and, as such, forms part of this disclosure. Through the use, pursuant to the invention, of the MALDI procedure, it is possible to obtain higher quality mass spectra. An ordinary individual skilled in the art would recognize that, in addition, the MALDI matrix may be first dosed on the hydrophilic areas and, therein, dried and that, thereupon, the to be analysed sample applied to the MALDI matrix and, again, dried and then analysed.

Furthermore, most preferably, the mass spectroscopic SIMS (Secondary Ion Mass Spectrometry) is that which is suggested to be used for these purposes, pursuant to the invention.

A preferred embodiment form of the SIMS is the TOF SIMS (Time of Flight Secondary Ion Mass Spectrometry), for instance, described in A. Benninghoven, Angew. Chem. Int. Ed. Engl. 33 1023 (1994). This publication is herewith listed as a reference and, as such, forms part of this disclosure.

A biomolecule, in the sense of the present invention, is any arbitrary molecule, in the course of the life cycle of any arbitrary virus or multicell organism, which is produced from this. Biomolecules contain at least one oxygen, nitrogen, sulphur, and/or phosphorus atom. Characteristic examples of biomolecules are: Spiegelmers, aptamers, ribozymes, peptides, polypeptides, proteins, antibodies, nucleic acids, nucleic acid analogs, DNA, double strand DNA, RNA, double strand RNA/DNA, vitamins, carbohydrates, hormones, glycopeptides, glycoproteins, lipids, fatty acids and cholesterol.

Biological material in the sense of the inventions contains at least one biomolecule. Hereby, however, it can also relate to large quantities of the same or different biomolecules. These may be presented in an unorganised manner one after the other or, based on interaction, construct functional units. Sample embodiments for this are protein complexes, genomes, cell cores, ribosomes, cells, cell assemblies, tissues or complete organisms.

With the MALDI PROCEDURE it is advantageous if the ultraphobic surface is conductive of electricity.

For the ordinary individual skilled in the art, it was found to be extraordinarily astonishing and not in accordance with expectations that, pursuant to this invention, mass spectra with high quality, good reproducibility and smaller measurement errors are to be obtained. The contamination of the sample to be analysed through the surface of the sample containers itself or through impurities on the surface of the sample containers, with use, pursuant to the invention, is strongly reduced. The procedure, pursuant to the invention, is simple to use and economical from a financial standpoint. Especially with MALDI mass spectrometry, the use, pursuant to the invention, proves itself to be advantageous.

The additional subject of the present invention is the use of preferably planar surfaces with hydrophilic and/or oleophilic areas, respectively, completely surrounded by ultraphobic areas, for the optical analysis of the samples.

Preferably, the surface is planar. Planar, in the sense of the invention, means that the surface exhibits the necessary ultraphobic properties in terms of surface topography, but does not exhibit any microvolumes in which liquid may be collected. Planar surfaces have, in particular, the advantage that manufacture is simple and that the liquid droplets need not, as known pursuant to the state of the art, be compressed in a microvolume or in an anchor area. Moreover, with planar surfaces, the influence on the liquid droplets lying thereon is very small and very few background signals are produced.

The surface may form a portion of any arbitrary surface formation or be thereupon arranged. Preferably, the surface formation will be a surface structure in the form of a plate, with an level surface, and quite preferably, the sample container surface has no indentations. Most preferably, a film, the surface of which exhibits respectively hydrophilic and/or oleophilic areas, completely surrounded by ultraphobic areas, will constitute the surface formation, pursuant to the invention.

The samples to be analysed, using the procedure pursuant to the invention, may contain any arbitrary substances, which are susceptible to optical analysis. Preferably the sample will, however, contain at least one biomolecule and/or biological material, very preferably, nucleic acids, nucleic acid analogs, Spiegelmers, aptamers, ribozymes, polypeptides, peptides and/or proteins. Preferably contained in the sample, in addition to the substances to be analysed, is at least one additional reagent. Furthermore, preferably the substances to be analysed are placed first in the hydrophilic and/or oleophilic areas and then, preferably, pressurized with at least one additional reagent, in order to analyze the reaction of the respective substance to be analysed with the respective reagent. Conversely it is naturally, in addition, conceivable that first different reagents are dosed on the hydro- and/or oleophobic areas and, thereupon, pressurized with the substances to be analysed.

The use pursuant to the invention is particularly well suited for optical detection procedures. The detection procedures may, thereby, encompass both special markings but can also work without markings. The use of reagents for marking of samples, which are given on a biochip is described, for instance, in "DNA Arrays: Technologies and Experimental Strategies", edited by Elena Grigorenko, CRC Press LLC (2002). This publication is herewith listed as a reference and, as such, forms a part of this disclosure. Fluorescence dyes, which are, for instance, well suited for the detection of interactions of samples with biochip immobilised probes are listed, for instance, in Handbook of Fluorescent Probes and Research Products of Molecular Probes. This publication is listed as a reference, and as such forms a part of this disclosure. In addition to the standard fluorescence procedure, use pursuant to the invention additionally extends to the detection of dyes which allow a specific time triggered fluorescence detection, such as, for instance, in Sauer M, Angerer B, Ankenbauer W, Folof the Papp Z, Gobel F, Han K T, Rigler R, Schulz A, Wolfrum J, Zander C, Single molecule DNA sequencing in submicrometer channels: state of the art and future prospects. J Biotechnol. 2001 Apr. 13; 86(3):181 201 and Bader B, Butt E, Palmetshofer A, Walter U, Jarchau T, Drueckes P. A cGMP dependent protein kinase assay for high throughput screening based on time resolved fluorescence resonance energy transfer. J Biomol Screen. 2001 August; 6(4):255 64.). These publications are hereby listed as a reference and as such form a part of this disclosure. Furthermore, use pursuant to the invention additionally encompasses the use of fluorescence resonance energy transfer systems, described in Bader et at (see above) and Oswald B, Gruber M, Bohmer M, Lehmann F, Probst M, Wolfbeis O S. Novel diode laser compatible fluorophores and their application to single molecule detection, protein labelling and fluorescence resonance energy transfer immunoassay. Photochem Photobiot. 2001 August; 74(2):237 45. and Kimball S R, Horetsky R L. Alterations in interprotein interactions between translation initiation factors assessed by fluorescence resonance energy transfer. Int J Biochem Cell Biol. 2001 August; 33(8):797 806.). These publications are hereby listed as a reference and, as such, form a part of this disclosure. The detection of fluorescence events using the sample container may be performed with standard commercial detectors, corresponding to the state of the art and is, for instance, mentioned in the book "DNA Arrays: Technologies and Experimental Strategies", edited by Elena Grigorenko, CRC Press LLC (2002)". This publication is listed hereby as a reference and, as such, forms a part of this disclosure. The detection of the sample container may, furthermore, occur through different standard procedures, such as those which are commonly used by an ordinary individual skilled in the art for the detection of fluorophores, in particular, common methods for the detection of fluorescence excitation through reflected light and transmitted light or evanescent fields. Photomultipliers, photodiodes and CCD cameras are appropriate for the detection. The use, pursuant to the invention, additionally encompasses the use of non fluorescent marking reagents. Such marking reactions additionally encompass the marking of biomolecules through different isotopes often used in molecular biological laboratories, such as, for instance, (superscript: 3) H, (superscript: 32) P, (superscript: 33) P and (superscript: 35) S and the detection of these through x-ray films or phosphor screens. A further use, pursuant to the invention, encompasses a detection procedure with marking reagents in the use and detection of luminescent dyes, such as CDP Star or similar luminophores. A typical application for the detection of hybridisation based hybridisation methods is found in Gold B, Radu D, Balanko A, Chiang C S. Diagnosis of Fragile X syndrome by Southern blot hybridization using a chemiluminescent probe: a laboratory protocol. Mol Diagn. 2000 September; 5(3): 1 69 78. This publication is hereby listed as a reference and, as such, forms a part of this disclosure. Furthermore encompassed is the marking free optical detection procedure, for instance, surface plasmon resonance, for instance as described in the article by Tokarska Schlattner M, Wallimann T, Schlattner U. entitled Related Articles to Multiple Interference of Anthracyclines with Mitochondrial Creatine Kinases: Preferential Damage of the Cardiac Isoenzyme and Its Implications for Drug Cardiotoxicity. Mol Pharmacol. 2002 March; 61(3):516 523 and the contained references therein. This article is hereby listed as a reference and, as such, forms a part of this disclosure.

It was exceedingly surprising and unanticipated for the ordinary individual skilled in the art that spectra with a high quality, good reproducibility and smaller measurement errors may successfully be obtained with use pursuant to the invention. The procedure, pursuant to the invention, is simple to use and economical from a financial standpoint. The use, pursuant to the invention, is strongly advantageous especially for the fluorescence analysis of biomolecules and/or biological material, as disruptive background signals are strongly reduced.

A further subject of the present invention is the use of preferably planar surfaces with hydrophilic and/or oleophilic areas, which are, respectively, completely surrounded by ultraphobic areas, for DNA sequencing with the help of the peptide nucleic acid (PNA) methodology.

For this use, the PNA molecules are immobilised on gold, silver, palladium and/or platinum and hybridised with single strand DNA. The DNA chain, which is hybridised on a single strand, may be detected through phosphate identification preferably with SIMS. Details of the procedures may found in the publication of H. F. Aarlinghaus et. al., Surf. Interface Anal. 33, 35 (2002), which is hereby listed as a reference and, as such, form a part of this disclosure.

The gold, silver, palladium and/or platinum preferably represent the hydrophilic and/or oleophilic area. This may be produced such that the gold, silver, palladium and/or platinum coat an ultraphobic surface. It is however also conceivable that the ultraphobic layer, in its layer construction, exhibits a gold, silver, palladium and/or platinum layer, which is then exposed on the corresponding area in order to produce the hydrophilic areas.

The use, pursuant to the invention, has the advantage, that the DNA requires no addition of dyes.

The following examples apply for all three uses pursuant to the invention.

Ultraphobic in the sense of the invention implies that the contact angle of a water and/or oil droplet, which lays on an ultraphobic surface, is more than 150°, preferably more than 160° and most preferably more than 170° and/or the roll off angle does not exceed 10°. The roll off angle is understood to be the angle of inclination of an essentially planar but structured surface against the horizontal, by which a standing water and/or oil droplet with a volume of 10 µl may be moved, based on the force of gravity, by means of tilting the surface. Such ultraphobic surfaces, are disclosed, for instance, in WO 98/23549, WO 96/04123, WO 96/21523, WO 00/39369, WO 00/39368, WO 00/39239, WO 00/39051, WO 00/38845 and WO 96/34697, which are hereby listed as a reference and, as such, form a part of this disclosure.

In a preferred embodiment, the ultraphobic areas demonstrate a surface topography with the local frequency of the individual Fourier components and their amplitude a(f) expressed through the integral $S(\log(f))=a(f).f$ calculated between the integration limits $\log(f_1/\mu m^{-1})=-3$ and $\log(f_2/\mu m^{-1})=3$ amounts to at least 0.3 and consists of a hydrophobic or, in particular, oleophobic material or are coated with a stable hydrophobation and/or, in particular, stable oleopbobation material. One such ultraphobic surface is described in the international patent application WO 00/39240, which is hereby listed as a reference and, as such, forms a part of this disclosure.

Hydrophilic and/or oleophilic areas in the sense of the invention are areas on which the water or oil droplets may be placed; i.e. a water or oil droplet hanging from a pipette system and brought in contact with the hydrophilic and/or oleophilic area, then remains hanging on the area and thus detaches from the pipette system. Preferably, a water or oil droplet, with a volume of 10 µl in the hydrophilic and/or oleophilic areas, takes on a contact angle <120°, preferably <110°, most preferably <90° and/or the roll off angle of this droplet exceeds 10°.

Pursuant to the invention, the surfaces of the respectively hydrophilic and/or oleophilic areas are completely surrounded by an ultraphobic area. Through this embodiment, it is possible to lay a liquid droplet in a strictly determined location and to anchor these comparatively firmly at that location.

Preferably, the surface is substantially ultraphobic and demonstrates a multitude of hydrophilic and/or oleophilic areas. The hydrophilic and/or oleophilic areas may be produced on the ultraphobic surface, for instance, through chemical and/or mechanical removal of at least a portion of the layer thickness of the ultraphobic layer, preferably by means of laser. Preferably the hydrophilic and/or oleophilic areas are, however, formed by way of a modification of only the uppermost molecular layer of the ultraphobic surface. Preferably, this modification is a mechanical and/or thermal ablation, by which preferably maximally one molecular layer of the ultraphobic surface is removed. Furthermore, the modification preferably proceeds through the thermal or chemical change of the ultraphobic surface, however, without removal, such as, for instance, as is described in DE 199 10 809 A1, which is hereby listed as a reference and, as such, forms a part of this disclosure. With this modification, the ultraphobic surface remains significantly unchanged in terms of its layer thickness. In a further preferred embodiment, the hydrophilic and/or oleophilic areas are reversibly producible on portions of the ultraphobic surface. Such surfaces and, respectively, procedures for reversible hydro- or oleophobation of portions of the ultraphobic surfaces are described in the German parallel application with the internal file number Sy 0029, which is hereby listed as a reference and, as such, forms a part of this disclosure.

The hydrophilic and/or oleophilic areas may exhibit any arbitrary form and size. Preferably, these have, however, a surface of 1 $\mu m^2$-10 $mm^2$. Such a surface allows a liquid droplet with a diameter of 5 nm-5 mm to settle thereupon and preferably to anchor such that it does not detach from the surface when hanging downwardly therefrom.

The use pursuant to the invention is well suited, in particular, in the area of research on bioactive compounds and in the area of biotechnology. This use is an additional subject of the present invention.

An additional subject of the present invention is a procedure for exact, contamination free dosing of preferably very small liquid volumes on surfaces with hydrophilic and/or oleophilic areas which are respectively completely surrounded by ultraphobic areas, in which the liquid to be dosed, preferably in the form of a droplet, is brought into contact with at least one hydrophilic and/or oleophilic area of the surface and then moved away such that the liquid to be dosed adheres to the hydrophilic and/or oleophilic area of the surface.

It was exceedingly surprising for the ordinary individual skilled in the art that it is possible with this procedure to dose a surface with liquid droplets of an exact, reproducible volume, without contamination of the liquid droplets by the surface. The procedure, pursuant to the invention, is simple to use and economical from a financial standpoint.

The volume of the liquid, which is brought into contact with the hydrophilic and/or oleophilic areas, must be at least as great as volume to be dosed. Preferably it is, however, significantly larger, such that liquid may be dosed on multiple hydrophilic and/or oleophilic areas.

The dosed liquid volumes result preferably from the dimensions of the hydrophilic and/or oleophilic areas and the liquid to be dosed. The larger the hydrophilic and/or oleophilic areas, the larger the dosed liquid droplets.

With reference to the hydrophilic and/or oleophilic areas, the ultraphobic surface and their production, the entire aforesaid disclosure holds true, an is thus is applicable to this aspect of the invention.

In the following, the invention is explained in greater detail with reference to the Examples 1-4 as well as FIGS. 1-5. This explanation is only by way of example and should not be interpreted as limiting the general inventive ideas.

EXAMPLE 1

Production of an ultraphobic surface:

A roll-polished AlMg3 sheet with a surface area of 26×76 $mm^2$ and a thickness of 0.15 mm is degreased at room temperature with chloroform (p.a.) followed by 20 seconds (s) in aqueous NaOH (5 g/l) at 50° C. Thereafter, it is prepickled for 20 s in $H_3PO_4$ (100 g/l), rinsed for 30 s in distilled water and electrochemically pickled for 90 s in a mixture of $HCl/H_3BO_3$ (each 4 g/l) at 35° C. and 120 $mA/cm^2$ at 35V AC voltage.

After 30 s rinsing in of distilled water and 30 s alkaline rinsing in aqueous NaOH (5 g/l), it was again rinsed for 30 s in distilled water and finally anodically oxidised for 90 s in $H_2SO_4$ (200 g/l) at 25° C. with 30 $mA/cm^2$ at 50 V DC voltage.

Thereafter it was rinsed for 30 s in distilled water, then for 60 s at 40° C. in $NaHCO_3$ (20 g/l) then again for 30 s in distilled water and dried for 1 hour at 80° C. in a drying cabinet.

The thus treated sheet is coated with an approximately 40 nm thick gold layer through cathode sputtering in high vacuum. Finally, the sample is coated with a monolayer through dipping for 24 hours in a solution of the thiol $CF_3$—$(CF_2)_7$—$(CH_2)_2$—SH in benzotrifluoride (p.a., 1 g/l) at room temperature in a closed container, followed by rinsing with benzotrifluoride (p.a.) and drying.

The surface demonstrates a static contact angle for water of 178°. With an inclination of the surface of <2°, a water droplet of volume 10 $\mu l$ rolls off.

EXAMPLE 2

A sample carrier with a surface according to Example 1 is used for this example. Various aliquots of MALDI matrices e.g. 3-hydroxypicolinic acid, sinapic acid and α-cyano-4-hydroxycoumarin acid dissolved in acetone, acetonitrile or a mixture of water and one of the mentioned organic solvents, where the solvent content should be at least 50% by volume, were dispensed on the uncleaned ultraphobic surface with a piezo dispensing station. After the rapid evaporation of the solvent, all the tested matrices precipitated on the ultraphobic surface as hydrophilic areas in the form of small crystals and adhered so firmly to it that they could not be detached with either a wipe or with compressed air. The places populated with matrices had respectively a diameter from 200-1000 $\mu m$. The locations covered with matrices are dosed, respectively, with 0.5-2.0 $\mu l$ different samples, containing biomolecules. The samples contain, for instance, peptides or proteins dissolved in 0.1% TFA (trifluoroacetic acid) water or oligonucleotides dissolved in a mixture of 50 vol. % water and 50 vol % acetonitrile, whereby the amount of biomolecules is, respectively, 0.1-1 pmol per $\mu l$. The samples are dosed on the matrices with a hand pipette and evaporated at room temperature and, then subsequently analysed in linear or reflector mode in a MALDI TOF mass spectrometer MTP Autoflex manufactured by the company Bruker Daltonik GmbH, 28359 Bremen. In all cases, reproducible mass spectra of higher quality are obtained, although the ultraphobic surface is not cleaned prior to the respective use. This is very important for the analysis of nucleic acids, where false readings may be obtained through the smallest contamination, for instance through Na or K salts on the sample carrier. Such contaminations may, indeed, materialize if sample carriers are left out for a period of time in normal laboratory air.

EXAMPLE 3

Example 3a

A Bruker 384/400 sample carrier manufactured by the company Bruker Daltonik GmbH, 28359 Bremen, which corresponds to the sample carriers of DE 197 54 978 A1, was intensively cleaned and, immediately prior to use, rinsed with highly pure double distilled water. The sample carrier is made of stainless steel and has an approximately 5 µm thick Teflon®-like coating, which is interrupted in 384 locations. The interruptions are regularly arranged across the sample carrier and have, respectively, a diameter of 400 µm. The stainless steel surface of the interruptions functions as a hydrophilic anchor for liquid droplets which are deposited on the surface of the sample carrier. 0.5 µl of a 50 mM solution of hydroxypicolinic acid in 50 vol. % acetonitrile/50 Vol. % water is pipetted onto this sample carrier and evaporated. After the evaporation of the solvent, the MALDI matrix exists as a crystalline layer substantially only on the hydrophilic anchors. On the locations covered with a MALDI matrix, 0.5 µl of a DNA 25mer oligonucleotide, dissolved in doubled distilled water, is respectively dosed, whereby the content of oligonucleotide is 1 pmol per µl. Finally, after evaporation of the solvent, a mass spectrum was determined in a MALDI TOF mass spectrometer MTP Autoflex, manufactured by the company Bruker Daltonik GmbH, 28359 Bremen. A representative result of this analysis is depicted in FIG. 1a.

Example 3b

The Example 3b corresponds substantially to the Example 3a, distinguished only in that, in this case, the sample carrier is left open but without being touched on a laboratory table in laboratory air for 12 hours after the intensive cleaning and before the rinsing with highly pure double distilled water. A representative result of this analysis is depicted in FIG. 1b.

Example 3c

In this example a sample carrier, with a surface as for Example 1 is used, the sample carrier being left open but without being touched on a laboratory table in laboratory air for 12 hours after the intensive cleaning and before the rinsing with highly pure double distilled water. The sample carrier is then dosed with acetonitrile droplets, respectively, with a volume of 0.1 µl and, respectively, at a distance of 4.5 mm apart. The acetonitrile droplets moisten the ultraphobic surface and serve as hydrophilic anchors (areas) of the MALDI matrix hydroxypicolinic acid (20 mM), which is dissolved in a mixture of 20 Vol. % acetonitrile/80 Vol. % water and, respectively, dosed as droplets with a volume of 0.5 µl directly on areas of the ultraphobic surface moistened with acetonitrile, before the acetonitrile has evaporated. The MALDI matrix solution moistens the ultraphobic surface. After the evaporation of the solvent, the MALDI matrix forms a crystalline layer. The crystalline matrices are, respectively, dosed with 0.5 µl of a DNA 25mer oligonucleotide, dissolved in double distilled water, whereby the content of oligonucleotide is 1 pmol per µl and this solution does not moisten the ultraphobic surface. After evaporation of the solvent, mass spectra were subsequently obtained in a MALDI TOF mass spectrometer MTP Autoflex, manufactured by the company Bruker Daltonik GmbH, 28359 Bremen. A representative result of this analysis is depicted in FIG. 1c. After the analysis, the sample carrier may be cleaned with an 80 Vol. % acetonitrile/20 Vol. % water mixture and then reused.

FIG. 1 shows, respectively, the representative results of experimental procedures 3a-c, whereby the letters associated with the spectra correspond to the letters of Example 3. The desired signals of the molecular ions peaks, in all three cases, are set at an intensity of 100 bel.units. In all three spectra, the desired signal $(M+H)^+$ dominates the single protonation and, therewith, the single positively charged free acid of the oligonucleotides. With the curves a and b, corresponding to the Examples 3a and 3b, at higher m/z values the signal, however, has satellite signals with a constant interval of m/z 22. The satellite signals show that, in addition to the desired molecular ion species, sodium associated molecular ions are also detected, which are known to indicate contamination of the samples through dust and, respectively, substances released due to humidity in the immediate surroundings. The curve c, which corresponds to Example 3c, shows the satellite signals, if at all, only in very reduced form. Satellite signals mean that the entire signal is distributed among multiple species and, therewith, the relationship between the actual signal and the background noise is impaired, in accordance with which the sensitivity of verification of the respective measurement is influenced negatively. In addition, satellite signals make the analysis of complex oligonucleotide mixtures more difficult, because the satellite signals can occasionally overlie the desired signals.

EXAMPLE 4

Example 4a

Using the aforementioned cleaned Bruker 384/400 sample carrier, liquid droplets with different DNA probes are dosed, and the sample carrier immobilised. The immobilised DNA sequences are hybridised with a Cy5 dye marked mixture of cDNAs. The hybridised cDNA is obtained from murine liver RNA through a reverse transcriptase reaction and the inclusion of the nucleotides marked with Cy5. The thus obtained liquid droplets were then analysed with a Genepix 4000 B device, manufactured by the company Axon Instruments, Union City, Calif., USA. The result of the analysis is depicted in FIGS. 2a, b, and c.

Example 4b

Figure 3:
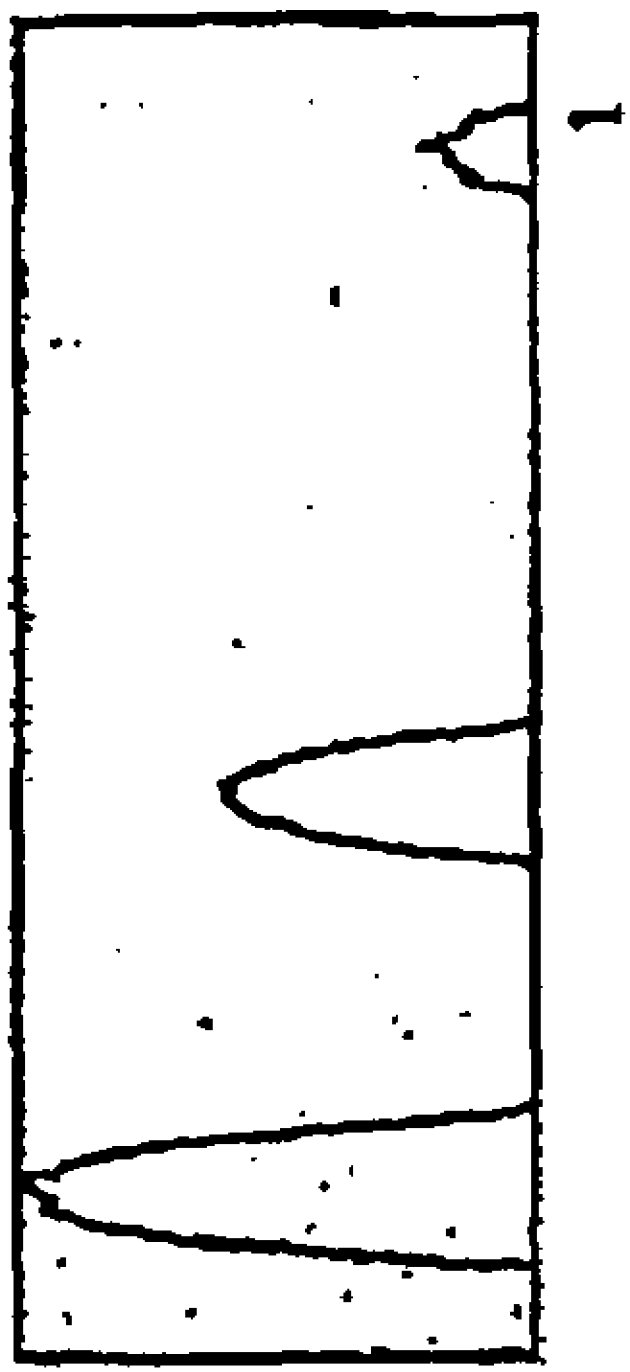
FIG. 3 shows a portion of the histogram (three liquid droplets) resulting from the experimental procedure pursuant to Example 4b.

In this example, the sample carrier having a surface as in Example 1 is used, on which acetonitrile droplets with a volume of 0.1 are respectively dosed at an interval of 4.5 mm to one another. The acetonitrile droplets moisten the ultraphobic surface and serve as hydrophilic anchors (areas) for liquid droplets with different DNA probes, which are respectively dosed directly on the acetonitrile moistened areas of the ultraphobic surface as droplets with a volume of 0.5 µl, before the acetonitrile is evaporated. The liquid droplets with different DNA probes do not moisten the ultraphobic surface. The thus immobilised DNA sequence is hybridised with a Cy5 dye marked mixture of cDNAs. The hybridised cDNA of murine liver RNA is obtained, through a reverse transcriptase reaction, and the inclusion of nucleotides marked with Cy5. The thus obtained liquid droplets are analysed with a Genepix 4000 B device, manufactured by the Axon Company. The result of the analysis is depicted in FIG. 3. The sample carrier is cleaned and reused after the analysis. The cleaning proceeds through washing with an acetonitrile/water mixture.

FIG. 2 shows the results of Example 4a. In FIG. 2a, the sample carrier is depicted. The light points represent liquid droplets, which are immobilised on the hydrophilic anchors. In FIG. 2b, four liquid droplets and their surroundings are depicted in enlarged scale. It is clearly to be seen that the immobilised liquid is not constrained to the areas of the hydrophilic anchors, rather that certain portions of the liquids, in addition, are located on the Teflon® surface. The more intensive and detailed analysis of the fluorescence image, illustrated by FIG. 2b, is represented in the form of a histogram, with related pixel values alongside the light regions in FIG. 2c. Ideally, fluorescence signals should only be produced where DNA has been put on the sample carrier, by which as a rule, a histogram results with peaks in regular intervals without the background signal. In the present case, however, a clear background signal can be seen between the peaks, that amounts to 10-20% of the overall signal strength and the precision of the analysis with the present mode of experimental procedure is limited.

FIG. 3 shows a portion of the histogram (three liquid droplets) resulting from the experimental procedure pursuant to Example 4b. It is clearly visible that the histogram has only three peaks in the area of the liquid droplets and exhibits no background noise. The signals are Gaussian and clearly separated from one another. A very precise analysis is thus obtainable by the experimental procedure. This is especially well illustrated by the histogram shown in FIG. 3, since the extreme right hand signal reaches only maximally 20% of the signal height of the other signals shown in the Figure and with no detectable background signal analogous to the one in FIG. 2b.

Figure 4:
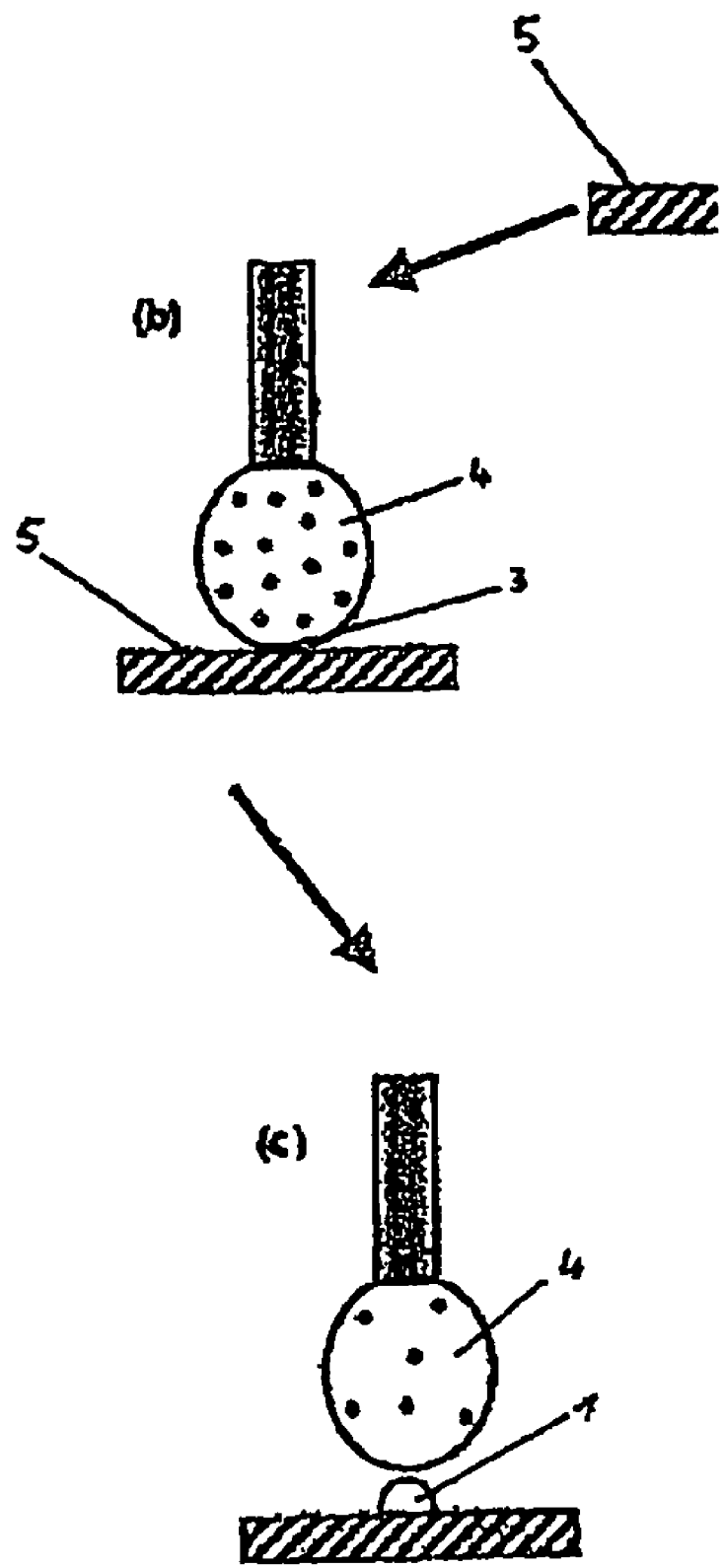
In FIG. 4, where the procedure of the invention is explained.

In FIG. 4, the procedure of the invention is explained. In FIG. 4a, a cross section of surface 2 of a sample carrier 6 is illustrated. Surface 2 demonstrates ultraphobic areas 5 and hydrophilic areas 3. On the ultraphobic areas 5, a 10 µl water droplet has a contact angle of >178° and a roll off of <2°. The hydrophilic areas 3 (only one is depicted) are completely surrounded by ultraphobic areas 5. On the hydrophilic areas 3, a 10 µl water droplet has a contact angle of <90° and a roll off angle of >10. In the present case, the hydrophilic area 3 in comparison to the ultraphobic areas 5 is represented in raised relief. An ordinary individual skilled in the art will recognize clearly that this is not the only scenario possible, but rather that the hydrophilic area 3, in addition, may align with the ultraphobic areas 5 or may be incorporated therein. In FIG. 4b is illustrated the manner in which a water droplet 4, which hangs from a pipette or a rod, is brought in contact with the hydrophilic area. Through the ultraphobicity of surface 5, which completely surrounds the hydrophilic area 3, the contact angle of the water droplet 4 is so large, that it touches only the hydrophilic area 3 and not the ultraphobic area 5. FIG. 4c shows the situation after the droplet 4 of the hydrophilic area is removed. A small portion 1 of the droplet 4 remains clinging to the hydrophilic area. The volume of liquid 1, which clings to the hydrophilic area, is proportional to these respective surfaces and very much smaller then the volume of the droplet 4, so that the dosing procedure, pursuant to the invention, may be repeated multiple times with a droplet 4.

Figure 5:
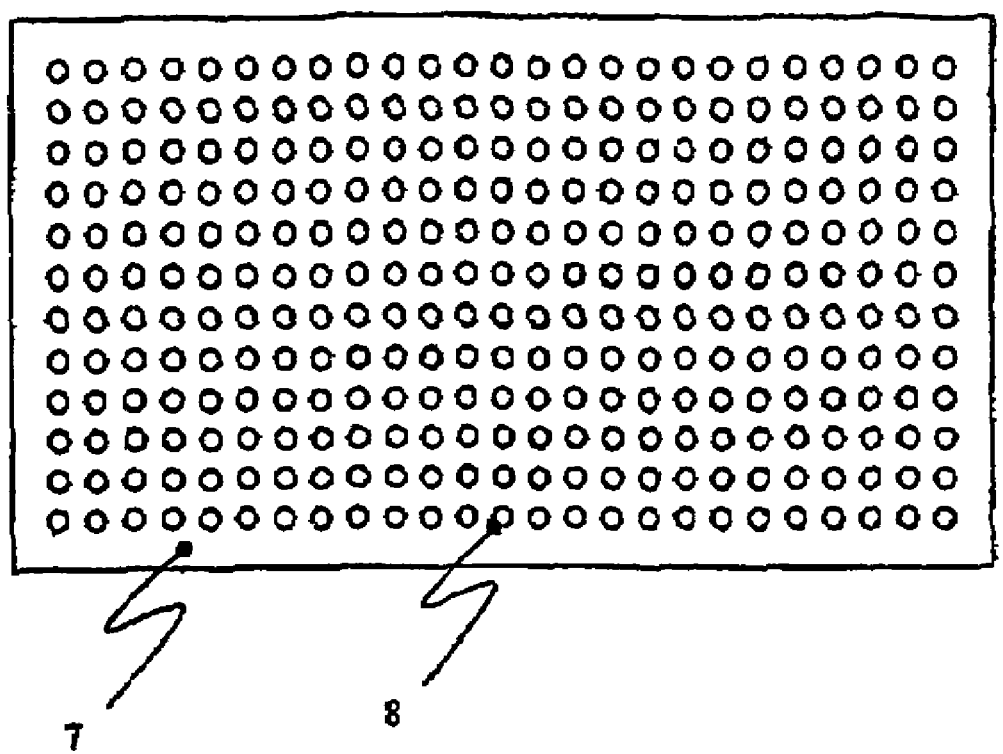

FIG. 5 shows an ultraphobic surface 7 with a multitude of hydrophilic areas 8, the surfaces of which are completely surrounded by the ultraphobic areas.

The invention claimed is:

1. A method of analyzing samples by mass spectroscopic analysis comprising providing a surface with hydrophilic and/or oleophilic regions, which are respectively completely surrounded by ultraphobic regions, on which the contact angle of a water and/or oil droplet, which lies on this surface, is less than 120° and the roll off angle of a water and/or oil droplet with a volume of 10 µl exceeds 10° and which is respectively surrounded by ultraphobic regions on which the contact angle of a water and/or oil droplet, which lies on this surface is more than 150° and the roll off angle of a water and/or oil droplet with a volume of 10 µl does not exceed 10°, applying a sample on the surface, which sample comprises a solvent, and analyzing the sample with a mass spectrometer.

2. The method of claim 1, characterized in that the surface is planar.

3. The method of claim 1, characterized in that the mass spectroscopic analysis is MALDI mass spectrometry.

4. The method of claim 3, characterized in that the ultraphobic surface is electrically conductive.

5. The method of claim 1, characterized in that the surface is substantially ultraphobic and has a multitude of hydrophilic and/or oleophilic regions.

6. The method of claim 1, characterized in that the hydrophilic or oleophilic regions are at least partly distributed across the surface pursuant to a defined pattern.

7. The method of claim 1, characterized in that the area of each hydrophilic region is $1 \mu m^2$-$10 mm^2$.

8. The method of claim 1, where the ultraphobic surface exhibits a surfaces topography, wherein the local frequency f of the individual Fourier components and their amplituteds a(f) expressed through the integral S(log (f))+a(f).f, calculated between the integration limits $\log(f1/\mu m-1)=-3$ and $\log(f2/\mu m-1)=3$, is at least 0.3, and the ultraphobic surface consists of hydrophobic and/or oleophobic materials and/or is provided with a coating of at least one hydrophobic and/or oleophobic material.

9. The method of claim 1, characterized in that one sample is respectively placed on the hydrophilic or oleophilic regions.

10. The method of claim 1, characterized in that the sample is biomolecular and/or biological material.

11. The method of claim 10 for analysis of nucleic acids, peptides or proteins.

12. The method of claim 1, where the hydrophilic and/or oleophilic regions are reversible.

13. The method of claim 1 in the research of active substances.

14. The method of claim 13, where hydrophilic and/or oleophilic regions are reversible.

* * * * *